United States Patent
Schaffer

(10) Patent No.: US 10,369,317 B2
(45) Date of Patent: Aug. 6, 2019

(54) CLIP-ON NASAL AIR HUMIDIFYING AND EPISTAXIS-PREVENTION DEVICE AND METHODS FOR USE WITH SUPPLEMENTAL OXYGEN

(71) Applicant: Scott Schaffer, Voorhees, NJ (US)

(72) Inventor: Scott Schaffer, Voorhees, NJ (US)

(*) Notice: Subject to any disclaimer, the term of this patent is extended or adjusted under 35 U.S.C. 154(b) by 412 days.

(21) Appl. No.: 15/158,431

(22) Filed: May 18, 2016

(65) Prior Publication Data

US 2016/0339199 A1 Nov. 24, 2016

Related U.S. Application Data

(60) Provisional application No. 62/163,262, filed on May 18, 2015.

(51) Int. Cl.

| A61M 16/06 | (2006.01) |
|---|---|
| A61M 16/14 | (2006.01) |
| A61M 16/16 | (2006.01) |
| A61M 16/00 | (2006.01) |
| A61M 16/10 | (2006.01) |

(52) U.S. Cl.
CPC .... *A61M 16/0672* (2014.02); *A61M 16/0666* (2013.01); *A61M 16/14* (2013.01); *A61M 16/142* (2014.02); *A61M 16/147* (2014.02); *A61M 16/16* (2013.01); *A61M 16/0003* (2014.02); *A61M 16/1045* (2013.01); *A61M 2202/0208* (2013.01)

(58) Field of Classification Search
CPC .............. A61M 16/00; A61M 16/0003; A61M 16/0461; A61M 16/0666; A61M 16/0672; A61M 16/0677; A61M 16/1075; A61M 16/109; A61M 16/16; A61M 16/14; A61M 16/142; A61M 16/147; A61M 2202/0208

USPC ....................................... 128/203.22, 207.18
See application file for complete search history.

(56) References Cited

U.S. PATENT DOCUMENTS

| 3,513,844 | A * | 5/1970 | Smith ............... | A61M 16/0666 |
|---|---|---|---|---|
| | | | | 128/207.18 |
| 4,156,426 | A * | 5/1979 | Gold ................. | A61M 16/0666 |
| | | | | 128/204.18 |
| 4,648,398 | A * | 3/1987 | Agdanowski ..... | A61M 16/0666 |
| | | | | 128/207.18 |
| 4,915,105 | A * | 4/1990 | Lee ........................ | A62B 18/00 |
| | | | | 128/205.27 |
| 5,105,807 | A | 4/1992 | Kahn et al. | |
| 6,354,293 | B1 | 3/2002 | Madison | |
| 9,750,915 | B2 * | 9/2017 | Opperman ........ | A61M 16/0666 |

(Continued)

FOREIGN PATENT DOCUMENTS

WO    WO-2016187359 A1    11/2016

OTHER PUBLICATIONS

International search report and written opinion dated Aug. 18, 2016 for PCT/US2016/033158.

*Primary Examiner* — Colin W Stuart
(74) *Attorney, Agent, or Firm* — Wilson Sonsini Goodrich & Rosati

(57) ABSTRACT

A disposable nasal air moisturizing device is removably attached to a nasal cannula to release a moisturizing liquid into a breathing gas and a patient's nasal airway. The intranasal sponges and moisturizing liquid prevents and treats both abrasions from the nasal cannula and excessive drying of the mucosa. This reduces the incidence of nosebleeds in patients using supplemental nasal oxygen.

13 Claims, 3 Drawing Sheets

(56) References Cited

U.S. PATENT DOCUMENTS

2010/0089395 A1     4/2010   Power et al.
2013/0333705 A1    12/2013   Opperman et al.

* cited by examiner

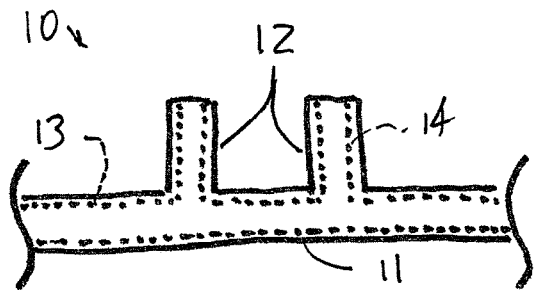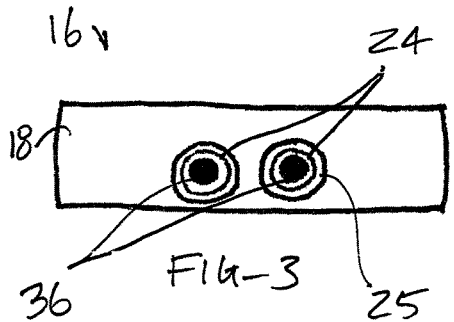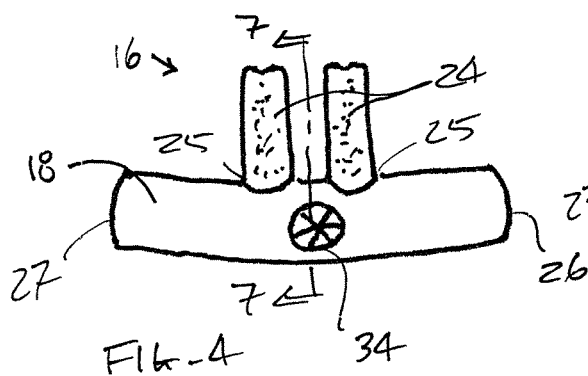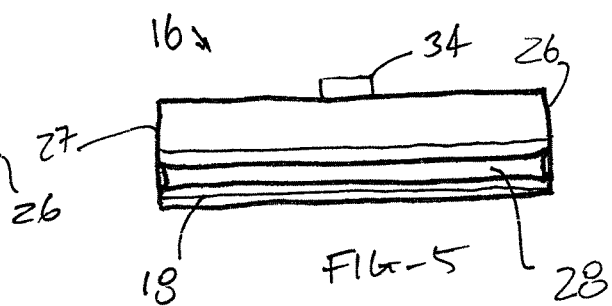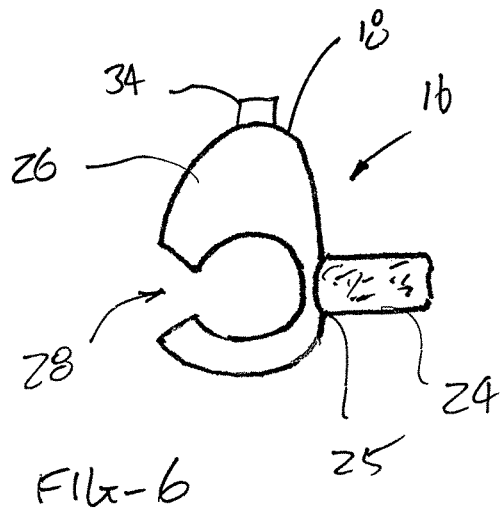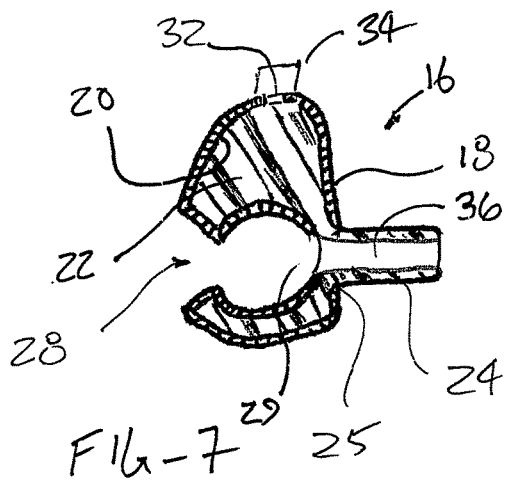

CLIP-ON NASAL AIR HUMIDIFYING AND EPISTAXIS-PREVENTION DEVICE AND METHODS FOR USE WITH SUPPLEMENTAL OXYGEN

CROSS-REFERENCE TO RELATED APPLICATION

The present application claims the benefit of provisional application No. 62/163,262, filed on May 18, 2015, the full disclosure of which is incorporated herein by reference.

BACKGROUND OF THE INVENTION

The invention relates generally to devices and methods for delivering moisture and/or other substances to the nasal passages concurrent with oxygen delivery using a nasal cannula, and more specifically to devices and methods for clipping or otherwise attaching a moisture saturation device onto a conventional nasal cannula.

A conventional nasal cannula 10 (FIG. 1) is a device used to deliver supplemental oxygen, air or other breathing gas mixture to a patient with respiratory, cardiac or hematologic disease. A conventional nasal cannula consists of a lightweight breathing tube 11 having two prongs 12 at one end. The two prongs are placed in the patient's nostrils to deliver the breathing gas. The other end of the tube is connected to a breathing gas supply, such as an oxygen tank or a wall connection in a hospital, via a flowmeter. The cannula may be attached to the patient by hooking the tube over the patient's ears. Typical adult nasal cannulas carry 1-5 liters of oxygen per minute while wider bore humidified nasal cannulas carry up to 60 liters of air/oxygen per minute. The nasal prongs typically contact the delicate mucosa of the nasal septum and turbinates, leading to ulceration The oxygen or air flowing from the gas source to the patient is usually very dry and can cause excessive drying of the mucosal membranes, discomfort, and in some cases ulceration of the nasal passage. Ulceration of the delicate nasal mucosa can cause nosebleed, or epistaxis which is especially serious in elderly patients who intentionally or unintentionally take medications or herbal supplements that thin their blood and impair normal blood clotting (aspirin, warfarin, apixaban eliquis, dabigatran etexilate pradaxa, edoxaban savaysa, rivaroxaban xarelto, fish oil, vitamin E, ginkgo, garlic capsules and others). Nasal ulcerations and bleeding in these patients can lead to respiratory problems, anemia and pain.

To address the problem of excessive nasal drying, it is common to pass the breathing gas through a chamber containing water or other fluid to increase the moisture content of the gas prior to delivery to the patient. However, such devices are often only minimally effective and do not prevent the direct abrasive effects of the nasal prongs irritating the delicate nasal mucosa.

U.S. Pat. No. 6,354,293 describes another approach to address the problem of dry nasal membranes. A humidifying element is placed retained under the user's nose, and oxygen or other gas is passed through the breathing humidifier into the users nostrils. The humidifying element is held between the nasal cannula and the nose, but is easily dislodged and can be dropped or lost, particularly with ambulatory patients.

For these reasons, it would be desirable to provide a nasal air humidifying device which can be clipped or otherwise removably attached to a conventional nasal cannulas to enhance humidification of the breathing gas and avoid direct abrasion of the delicate nasal mucosa by the nasal prongs of supplemental oxygen.

SUMMARY OF THE INVENTION

A nasal air moisturizing or humidifying device is configured to be securely and removably attached, typically clipped, over the oxygen delivery prongs of a conventional nasal cannula. The nasal air moisturizing device includes a sponge or other liquid-absorbable material configured to cover the prongs of the nasal cannula. The sponge will be saturated with saline or other a moisturizing fluid to continuously release moisture into the breathing gas being delivered to the patient. The sponge-like material will also provide an atraumatic interface with the nasal mucosa to avoid direct trauma and abrasion of the mucosa by the nasal prongs.

In specific embodiments, the nasal air moisturizing device comprises a shell or frame body that carries saline or other moisturizing fluid which can be clipped or otherwise attached over the nasal cannula. The external shell or frame encloses a sponge for holding saline or other moistening fluid. The moisture absorbent sponge or other material is also carried in the shell and is configured (a) to be positioned over the nasal prongs of the conventional nasal cannula when the shell is attached to the breathing tube and (b) to receive moisturizing liquid and release the moisturizing liquid into breathing gas being delivered through the prongs by diffusion or capillary action.

The frame typically comprises a rigid shell having an interior volume. The reservoir and the moisture absorbent material are usually disposed within the interior volume of the shell. The moisture absorbent material will usually comprise a sponge-like material or a gauze-like material and will includes two protrusions which extend outwardly through apertures in the shell. The two protrusions will extend outwardly through apertures in the shell and will have passages which are configured to be disposed over the prongs when the when the shell is attached to the nasal cannula. Typically, the sponge or other moisture absorbent material will be at least partially disposed within the shell with the protrusions extending outwardly from the shell so they can enter the patient's nose.

The present invention also provides methods for establishing an interface between a nasal cannula and a patient's nasal mucosa. The method comprises providing a conventional nasal cannula of the type having prongs suitable without modification for placement in the nostrils of a patient for delivering a breathing gas to the patient. Such a conventional nasal cannula, when used without the methods and devices of the present invention, will suffer from the short comings discussed above. To overcome these shortcomings, and in accordance with the present invention, a moisture absorbent material is placed around the prongs of the nasal cannula, and the prongs of the nasal cannula are positioned in the patient's nostril so that the moisture absorbent material provides a moisture permeable barrier between the prongs and mucosa of the patient's nostrils. As a breathing gas is delivered to the patient's nostrils through the prongs of the nasal cannula, the moisture is drawn from the intranasal sponges and nasal air is humidified. The moisture in the intranasal sponges is maintained by refilling the sponge or reservoir with saline or other moisturizing medical solution through the port on the top of the shell.

In specific aspects of the methods, the moisture retaining sponges or other materials between the prongs and mucosa will inhibit and often eliminate abrasion of the nasal septum and nasal turbinates in addition to moisturizing the mucosa, and the methods are suitable for treating patients already suffering from septal ulceration and nosebleeds. The moisture absorbent material typically comprises a sponge or gauze body having protrusions, and the protrusions are typically placed over the prongs of the nasal cannula. The sponge body is then connected to the reservoir, and the protrusions are then inserted into the nostrils together with the nasal cannula. The methods may further comprise filling the reservoir with the moisturizing liquid after the nasal cannula has been placed on the patient. The reservoir is typically filled with a nasal saline solution and/or a bacteriostatic/bacteriocidal solution, and the reservoir may be replenished periodically without removing it from the patient. Moreover, the assembly of the shell, the moisture absorbent material, and the reservoir may be periodically replaced or exchanged without replacing the nasal cannula.

Although the nasal air moisturizing devices of the present application are illustrated as integrated or monolithic devices without moving parts, it would also be possible to utilize spring-loaded or other articulated clips which could be removably secured over the nasal cannulas.

BRIEF DESCRIPTION OF THE DRAWINGS

FIG. 2 is a detailed view of the prongs of the conventional nasal cannula of FIG. 1.

FIG. 3 is a top view of a nasal air humidifying device of the present invention.

FIG. 4 is a front view of the nasal air humidifying device of the present invention.

FIG. 5 is a back view of the nasal air humidifying device of the present invention.

FIG. 6 is a side view of the nasal air humidifying device of the present invention.

FIG. 7 is a cross-sectional view of the nasal air humidifying g device of the present invention taken along line 7-7 of FIG. 4.

DETAILED DESCRIPTION OF THE INVENTION

Figure 1:
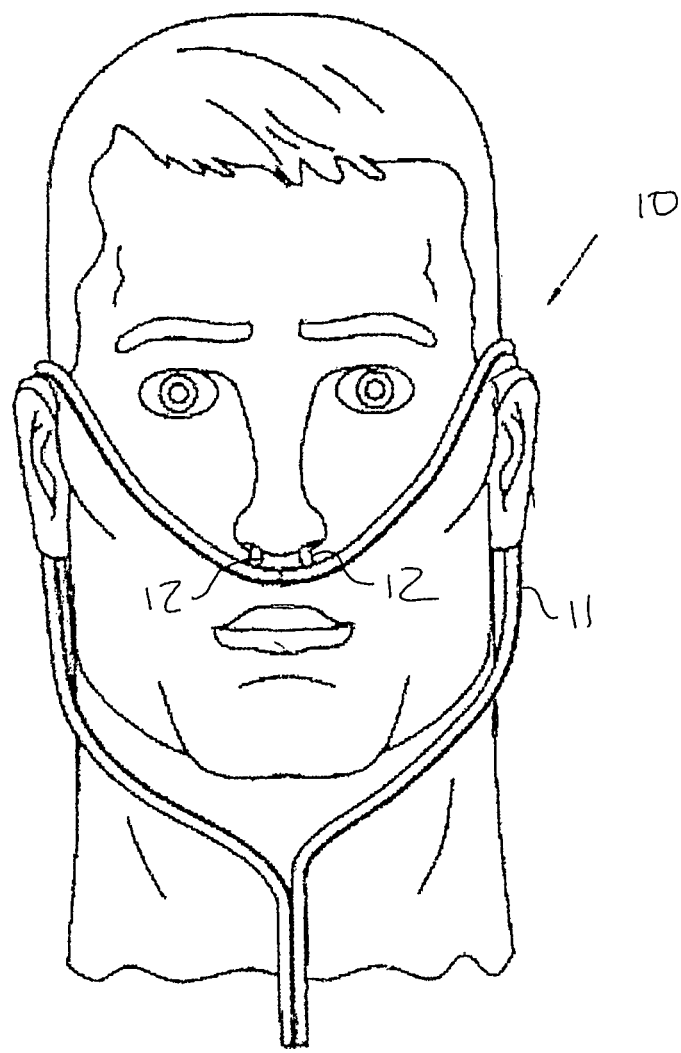
FIG. 1 illustrates a conventional nasal cannula in place with prongs in a patient's nose.

A disposable device is described which clips or otherwise attaches onto a conventional, commercially available supplemental nasal oxygen cannula to moisturize the nasal mucosa as the patient breaths oxygen being delivered by the cannula. This device reduces/prevents nosebleeds associated with the use of supplemental oxygen. The device structure typically includes a sponge or other liquid absorbing material or mass and is designed to clip over the nasal prongs of a supplemental oxygen cannula. Common nasal saline solution or bacteriostatic/bactericidal solution can be used to moisturize the nasal sponges, and oxygen flowing through the nasal prongs carries the moisture from the sponge to the nasal membranes. In addition, the sponge typically covers the nasal prongs and releases or transfers the saline or other moisturizing liquid directly into the nasal air and further holds the prongs away from the nasal septum, minimizing or preventing ulceration of the delicate nasal mucosa.

A major benefit of the device of the present invention is its compatibility with existing medical equipment. The ability to continue use of a familiar nasal cannula design improves compliance and reduces the financial burden of purchasing completely new oxygen delivery devices. The reservoir of the device may be filled with sterile normal saline solution, typically available in hospitals, nursing homes and pharmacies.

Bacteriostatic or bactericidal solution can also be used to fill the reservoir, if the clinical condition of the patient warrants.

The learning curve of use is short. Families and healthcare workers can understand the easy clip-on properties of this device, and can successfully use it almost immediately.

The device is made as a simple shell with a slot or clip at the bottom, and there is only one way that the nasal oxygen can be inserted into the device, and that immediately creates a firm or tight seal.

The device is disposable to reduce bacterial/viral/fungal contamination.

Referring now to the drawings, FIG. 2 shows more detail of a conventional nasal cannula 10 of the type that can be used with the devices and methods of the present invention. In particular, the conventional nasal cannula 10 includes a breathing tube 11 and has an internal lumen 13 which receives a flow of oxygen or other breathing gas from a breathing gas source, such as a pressure bottle or a wall connector. The internal lumen 13, in turn, opens to lumens 14 formed through the prongs 12 which are received in the patient's nostrils, as better seen in FIG. 8 which will be described later.

Referring now to FIGS. 3-7, a nasal air humidifying device 16 constructed in accordance with the principles of the present invention comprises a shell 18 defining an interior space 20 (FIG. 7). The shell 18 may be formed from a soft or hard plastic or other conventional medical device material, typically by molding or thermal forming. A moisture absorbent material 22 (FIG. 7), typically a sponge, gauze, or other conventional medical material used to absorb medical grade solutions, is present within the interior 20 of the shell 18 and includes a pair of protrusions 24 which extend outwardly from the shell through apertures 25 formed in a front surface of the shell. A slot 28 is formed in a lower portion of a back wall of the shell, as best seen in FIGS. 5, 6 and 7, to accommodate the breathing tube 11 when the prongs 12 are placed into and through passages 36 in the protrusions 24.

Figure 8:
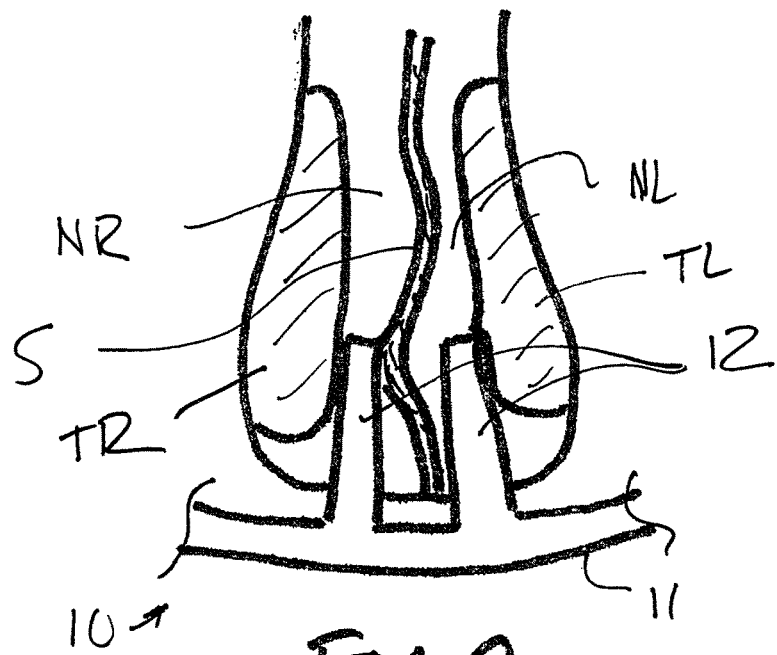
FIG. 8 illustrates the prongs of the conventional nasal cannula of FIG. 1 present in the patient's nostrils.
Figure 9:
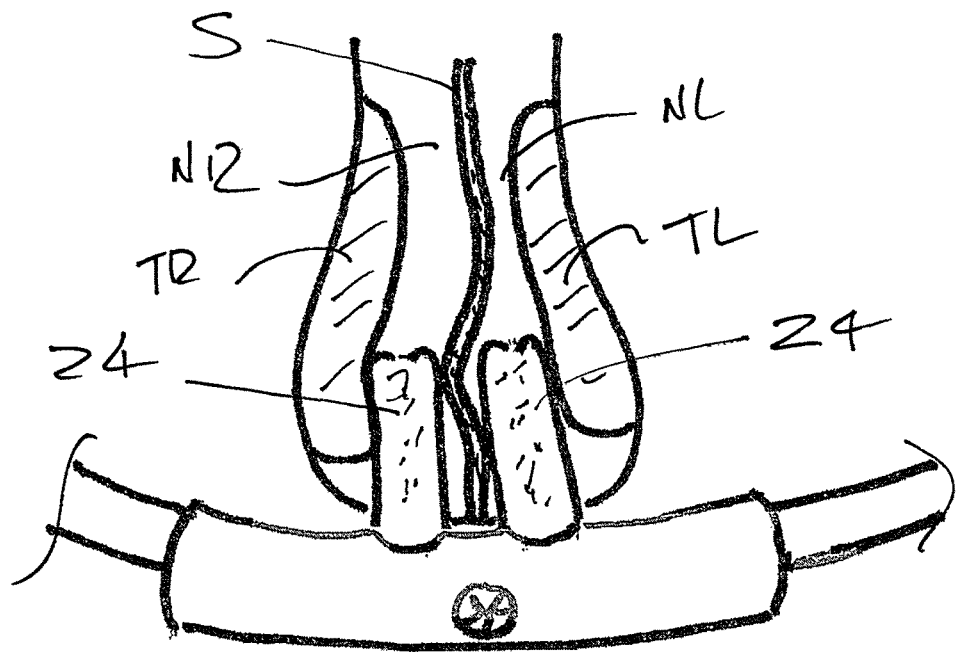
FIG. 9 illustrates the nasal air humidifying device of the present invention covering the prongs of a conventional nasal cannula present in the patient's nostrils.

Referring now to FIGS. 8 and 9, the nasal cannula 10 without benefit of the present invention (FIG. 8) may be placed in a patient's nostrils so that one prong 12 enters the right nostril NR and the other prong enters the left nostril NL. The prongs are exposed within the nasal cavity and rub against the mucosa of the septum S and turbinates T. As discussed above, such unprotected rubbing can abrade and damage the mucosal surfaces of the nasal cavity. In addition, the air entering the nostrils is dry and can have the other deleterious effects described above. The shell 18 has right and left sidewalls 26 and 27, respectively, so that the shell will usually define a complete enclosure for the moisture absorbent material 22 except for (1) a port 32 (FIG. 7) with a cover 34 that allows for liquid introduction into the moisture absorbent material 22 and (2) apertures 25 and 29 (FIG. 7) that allow the protrusions 24 to extend outwardly from the shell 18.

The shell 18 thus encloses moisture absorbent material 22 to define a reservoir region in its interior so that the moisturizing liquid can be introduced through port 32 into the reservoir region where it is absorbed by the moisture absorptive material. The moisturizing liquid will distribute through the moisturizing absorbent material 22 and is able to travel upward through the protrusions 24 and into the patient's nostrils by capillary action. In this way, moisture which is carried into and released from the protrusions 12 will help humidify the breathing gas and moisturize the mucosal surfaces within the patient's nostrils as the otherwise dry air is introduced through the prongs 12.

As shown in FIG. 9, the breathing tube 11 has been inserted through the slot 28 of the nasal air humidifying device 16. More specifically, the breathing tube 11 is inserted through the slot 28 of the shell 18 so that the prongs 12 pass through the apertures 25 and 29 and through the passages 36 of the protrusions 24. After placement into the nostrils NL and NR, the protrusions 24 directly engage the surfaces of the turbinates TL and TR as well as the septum S, where they act both as a protective barrier to inhibit abrasion and to deliver moisture to humidify the air being delivered to the patient.

What is claimed is:

1. A nasal air moisturizing device to be used with a nasal cannula having a pair of prongs for delivering gas to a patient's nostrils, said device comprising:
    an outer shell having an interior volume and a pair of apertures positionable over the pair of prongs of the nasal cannula; and
    a moisture absorbent material having a portion positioned within the interior volume of the shell and a pair of protrusions extending outwardly through the pair of apertures of the shell, wherein the protrusions are positioned over the pair of prongs of the nasal cannula when the shell is attached to the nasal cannula, wherein a portion of the moisture absorbent material positioned within the shell is configured to receive moisturizing liquid and the pair of protrusions of the moisture absorbent material are configured to be positioned in the patient's nostrils to release the moisturizing liquid into breathing gas being delivered through the pair of prongs.

2. The nasal air moisturizing device as in claim 1, wherein the interior volume is configured to hold a moisturizing liquid, wherein the moisture absorbent material receives moisturizing liquids.

3. The nasal air moisturizing device as in claim 1, wherein the two protrusions which extend outwardly through apertures in the shell have passages therethrough which are configured to be disposed of the pair of prongs when the shell is attached to the nasal cannula.

4. The nasal air moisturizing device as in claim 1, wherein the moisture absorbent material is at least partially disposed within the shell with protrusions extending outwardly through the shell.

5. The nasal air moisturizing device as in claim 1, wherein the moisture absorbent material comprises a sponge.

6. A method for providing an interface between a nasal cannula and a patient, said method comprising:
    providing a nasal cannula having prongs suitable without modification for placement in the nostrils of a patient for delivering a breathing gas to the patient;
    placing an assembly comprising a shell having an interior volume, a pair of apertures and a moisture absorbent material within the interior volume over the prongs of the nasal cannula, wherein the prongs extend from the interior of the shell through the apertures to an exterior of the shell and are covered by protrusions of the moisture absorbent material;
    positioning the protrusions of the moisture absorbent material which cover the prongs of the nasal cannula in the patient's nostrils so that the moisture absorbent material provides a moisture permeable barrier between the prongs and mucosa of the patient's nostrils;
    delivering a breathing gas to the patient's nostrils through the prongs of the nasal cannula; and
    wherein the moisture absorbent material contains a moisturizing liquid, wherein the moisture absorbent material releases the moisturizing liquid into the mucosa and the breathing gas to inhibit drying of the nasal mucosa.

7. The method of claim 6, wherein the moisture permeable barrier between the prongs and mucosa inhibits or prevents abrasion of the nasal septum and nasal turbinates.

8. The method of claim 6, wherein the patient is suffering from septal ulceration and nosebleeds from prior use of supplemental oxygen.

9. The method of claim 6, wherein the protrusions are inserted into the nostrils together with the nasal cannula.

10. The method of claim 9, further comprising introducing the moisturizing liquid into the shell through a port after the nasal cannula has been placed on the patient.

11. The method of claim 10, wherein a nasal saline solution and/or a bacteriostatic/bacteriocidal solution is introduced through the port.

12. The method of claim 10, wherein the moisturizing liquid is introduced into the shell through a port periodically without removing the shell from the patient.

13. The method of claim 9, further comprising replacing the assembly of the shell and the moisture absorbent material over the nasal cannula without replacing the nasal cannula.

* * * * *